United States Patent [19]

Sachtler et al.

[11] Patent Number: 4,939,110
[45] Date of Patent: Jul. 3, 1990

[54] CATALYST FOR THE ISOMERIZATION OF AROMATICS

[75] Inventors: J. W. Adriaan Sachtler, Des Plaines; R. Joe Lawson, Palatine, both of Ill.

[73] Assignee: UOP, Des Plaines, Ill.

[21] Appl. No.: 394,038

[22] Filed: Aug. 14, 1989

Related U.S. Application Data

[62] Division of Ser. No. 259,086, Oct. 17, 1988, Pat. No. 4,899,012.

[51] Int. Cl.$^5$ .............................................. B01J 29/28
[52] U.S. Cl. .......................................... 502/66; 502/71
[58] Field of Search ..................... 502/66, 71, 74, 77

[56] References Cited

U.S. PATENT DOCUMENTS

| | | | |
|---|---|---|---|
| 3,554,900 | 1/1971 | Bowes | 208/111 |
| 3,751,502 | 8/1973 | Hayes et al. | 260/668 A |
| 3,821,105 | 6/1974 | Mitsche et al. | 502/66 |
| 3,827,971 | 8/1974 | Kominami et al. | 208/139 |
| 3,827,988 | 8/1974 | Kominami et al. | 252/441 |
| 3,839,195 | 10/1974 | Wilhelm | 208/139 |
| 3,887,495 | 6/1975 | Juguin et al. | 252/464 |
| 3,894,104 | 7/1975 | Chang et al. | 260/668 R |
| 4,116,870 | 9/1978 | Weisang et al. | 252/439 |
| 4,152,363 | 5/1979 | Tabak et al. | 585/481 |
| 4,234,697 | 4/1982 | Lewis et al. | 502/66 |
| 4,331,822 | 5/1982 | Onodera et al. | 585/482 |
| 4,394,300 | 7/1983 | Chu et al. | 502/77 |
| 4,485,185 | 11/1984 | Onodera et al. | 502/71 |

Primary Examiner—Carl F. Dees
Attorney, Agent, or Firm—Thomas K. McBride; John F. Spears, Jr.; Richard E. Conser

[57] ABSTRACT

An improved catalyst is disclosed for the conversion of aromatic hydrocarbons which comprise a Group VIII metal, lead, a pentasil zeolite, and an inorganic oxide binder, wherein 80–100% of the Group VIII metal and 60–100% of the lead are contained on the binder. An alkylaromatic isomerization process also is disclosed which is particularly effective for the conversion of ethylbenzene without substantial loss of xylenes.

12 Claims, 1 Drawing Sheet

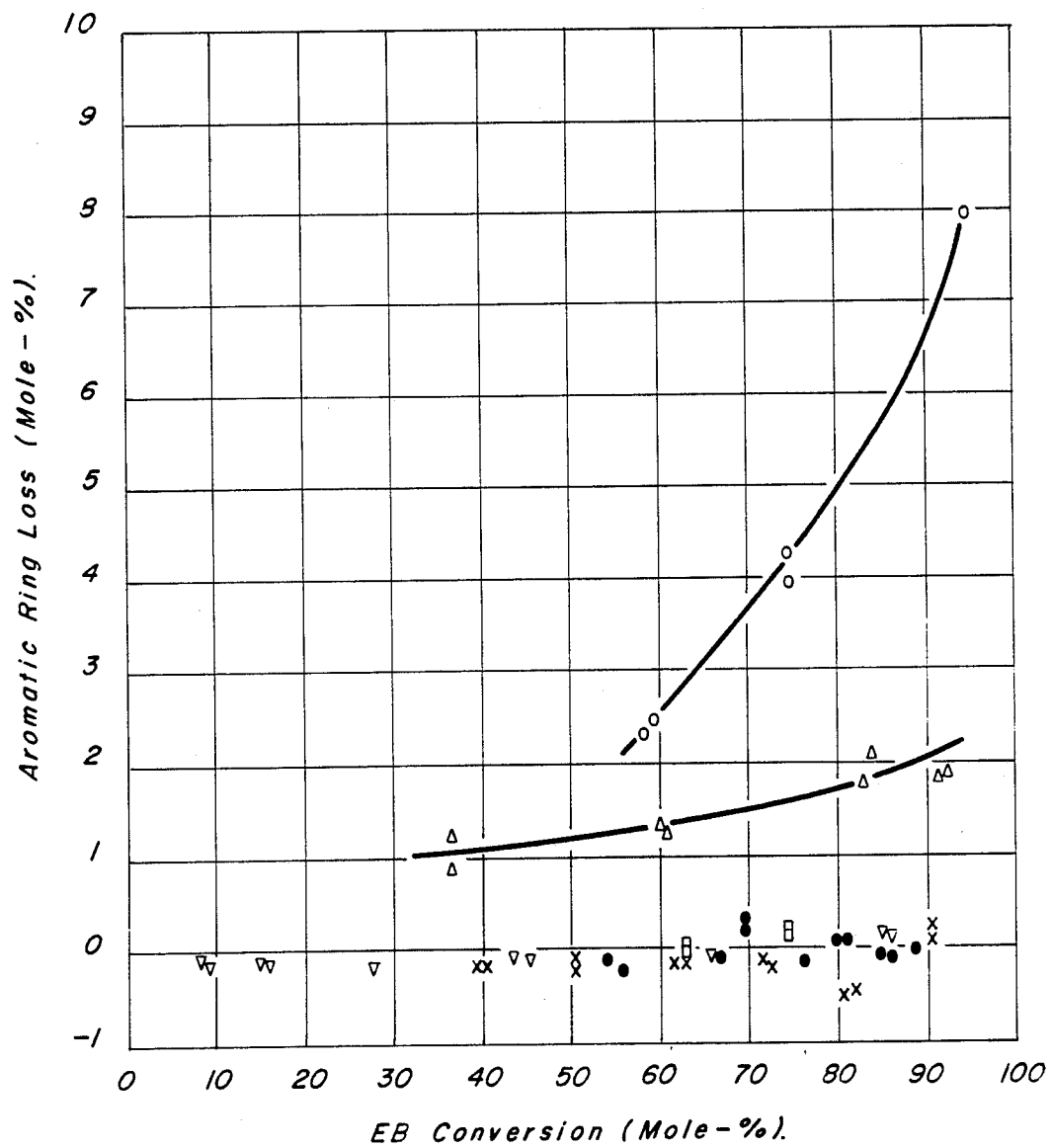

CATALYST FOR THE ISOMERIZATION OF AROMATICS

This application is a Divisional application of prior copending application Ser. No. 259,086 filed Oct. 17, 1988, now U.S. Pat. No. 4,889,012.

BACKGROUND OF THE INVENTION

Field of the Invention

This invention relates to an improved catalyst useful in the conversion of aromatic hydrocarbons, particularly for the isomerization of alkylaromatics.

General Background

Bound zeolite catalysts are widely used for hydrocarbon conversion reactions, based on their high activity and/or selectivity. Such catalysts are particularly useful in conversions involving aromatic hydrocarbons: synthesis of aromatics from paraffins and naphthenes, alkylation of aromatics with light olefins, transalkylation and isomerization. A major driving force in the development of synthesis, transalkylation and isomerization catalysts has been the growth in demand for para-xylene as an intermediate in polyester manufacture.

$C_8$ aromatics which have been synthesized and recovered in an aromatics complex contain a mixture of the three xylene isomers and ethylbenzene. Para-xylene normally is recovered in high purity from the $C_8$ aromatics, for example by adsorption or crystallization, and other isomers may be separated as well. Para-xylene generally constitutes only 15–25% of the mixture, but accounts for most of the demand for $C_8$ aromatics. Normally, it is desirable to minimize the amount of feedstock required for a given quantity of para-xylene. Therefore, it is industrially significant to isomerize the para-depleted raffinate from para-xylene recovery to adjust the isomer balance toward thermodynamic equilibrium for recycle to the recovery section.

An increasingly close approach to equilibrium of $C_8$ aromatic isomers in an isomerization process is associated with higher losses of $C_8$ aromatics to other hydrocarbons. A close approach to equilibrium minimizes the amount of recycle to para-xylene recovery, and thus reduces the investment and operating costs of the complex. A lower loss of $C_8$ aromatics reduces feedstock requirements and increases the proportion of higher-value products. The performance of an isomerization catalyst is assessed principally by the balance of $C_8$ aromatic losses for a given approach to equilibrium and by its stability while achieving such performance.

Numerous catalysts for isomerizing $C_8$ aromatics have been disclosed, and many of them involve the use of a crystalline aluminosilicate zeolite-containing catalyst. Crystalline aluminosilicates, generally referred to as zeolites, may be represented by the empirical formula:

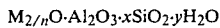

$$M_{2/n}O \cdot Al_2O_3 \cdot xSiO_2 \cdot yH_2O$$

in which n is the valence of M and x is generally equal to or greater than 2.

Zeolites have skeletal structures which are made up of three-dimensional networks of $SiO_4$ and $AlO_4$ tetrahedra, corner linked to each other by shared oxygen atoms. Zeolites particularly suited for use as isomerization catalysts include mordenite and the ZSM variety. In addition to the zeolite component, certain metal promoters and inorganic oxide matrices have been included in isomerization catalyst formulation. Examples of inorganic oxides include silica, alumina, and mixtures thereof. Metal promoters, such as those of Group VIII or Group III metals of the Periodic Table, have been used to provide a dehydrogenation functionality. The acidic function can be supplied by the inorganic oxide matrix, the zeolite, or both.

Catalysts for isomerization of $C_8$ aromatics ordinarily are characterized by the manner of processing ethylbenzene associated with the xylene isomers. Ethylbenzene is not easily isomerized to xylenes, but it normally is converted in the isomerization unit because separation from the xylenes by superfractionation or adsorption is very expensive. In older isomerization technology, ethylbenzene was transalkylated with resulting product loss to heavy aromatics.

One modern approach is to react the ethylbenzene to form a xylene mixture in the presence of a solid acid catalyst with a hydrogenation-dehydrogenation function. An alternative approach is to dealkylate ethylbenzene to form principally benzene while isomerizing xylenes to a near-equilibrium mixture. The former approach enhances xylene yield by forming xylenes from ethylbenzene, but the latter approach commonly results in higher ethylbenzene conversion and thus lowers the quantity of recycle to the para-xylene recovery unit. The latter approach also yields a high-quality benzene product. The effectiveness of a catalyst applied in the latter approach thus is measured by:

activity, in approaching an equilibrium mixture of xylene isomers, and achieving ethylbenzene conversion, and selectivity in both xylene isomerization and ethylbenzene conversion, minimizing side reactions such as transalkylation, disproportionation, demethylation, and hydrogenation and subsequent cracking of the aromatic ring.

In particular, the ethylbenzene conversion should yield benzene and ethane rather than transalkylating the ethyl group to another aromatic ring. The catalyst of the present invention is applied to advantage in this approach.

Prior Art

The prior art is replete with references to catalysts containing zeolites and/or multiple metals useful for hydrocarbon conversions, some of which disclose the utility of such catalysts for the isomerization of $C_8$ aromatics.

U.S. Pat. No. 3,554,900 (Bowes) teaches a method of treating a zeolite containing a catalytically active metal on its surface with a poisoning metal without affecting the catalytic activity of the interior of the zeolite. The catalytically active metal may be platinum and the poisoning metal may be lead. The compositing of the metals with the zeolite and the subsequent contacting of the support by the poisoning metal is in contradistinction to the present invention, however, and Bowes does not teach a halogen compound or a binder. Further, Bowes discloses a hydrocracking process in a preferred embodiment which contrasts with the preferred use of the present invention.

U.S. Pat. No. 3,751,502 (Hayes et al.) discloses an isomerization process employing a catalyst comprising a platinum-group metal, a Group IV-A metallic component, and a halogen component on a carrier containing alumina and a crystalline aluminosilicate. The preferred aluminosilicate is mordenite, however, and faujasite is also taught; there is no indication that a pentasil zeolite was contemplated. Further, Hayes et al. teaches a preferred lead to platinum ratio of 0.05 to 0.9 in contradistinction to the present invention.

U.S. Pat. Nos. 3,827,971 and 3,827,988 (Kominami et al.) teach a process for producing aromatic hydrocarbons and a catalyst composition, respectively, comprising platinum, lead, another metal from a list of 25, and chlorine on a carrier such as silica-alumina, alumina hydrate, silica, zeolite, kaolin, acid clay or bentonite. Selecting the present catalyst from the myriad possibilities of Kominami et al. would be analogous to locating a needle in a haystack. Kominami et al. '971 is distinguished from the present invention in teaching a lower ratio of lead to platinum, 0.1 to 1.5. Kominami et al. '988 teaches a generally lower range of ratios, 0.3 to 2.5, than the present invention. Further, the examples comparing aromatics production in relation to lead/platinum ratio show less favorable results with higher ratios. Kominami et al. '971 and '988 both teach a catalyst that suppresses isomerization, supporting the above distinctions in composition relative to the present catalyst.

U.S. Pat. No. 3,839,195 (Wilhelm) discloses a catalytic reforming process employing a catalyst composing a platinum-group metal, lead, and a halogen component on a porous carrier, preferably alumina. A zeolitic crystalline aluminosilicate is taught in the general disclosure. Wilhelm restricts the atomic ratio of lead to platinum to 0.05 to about 0.9:1, however, in contradistinction to the lead:platinum ratio of 2:1 to 10:1 in the more specifically defined zeolitic composite of the present invention.

U.S. Pat. No. 3,887,495 (Juguin et al.) discloses a catalyst, applied in the dehydrogenation of paraffins, consisting essentially of alumina and two or more metals. Metals disclosed are rhenium plus at least one of lead, gallium, indium, thallium, germanium, tin, antimony and bismuth, or at least one each of Group VIII, plus molybdenum and tungsten, plus gallium, indium, thallium, germanium, antimony and bismuth. Juguin et al. does not teach a Group VIII metal plus lead on the same catalyst, however, and is silent with respect to the incorporation of a zeolite on the catalyst composite. Further, Juguin et al. teaches a substantially neutral catalyst in contradistinction to the present invention.

U.S. Pat. 3,894,104 (Chang et al.) discloses a process for aromatization of feedstocks containing heteroatoms using a zeolitic catalyst containing at least one metal of Groups IB, IIA, IIB, IIIA, IVA, and VIII. These groups would include lead along with the Group VIII metals, but only magnesium, calcium, copper, zinc, cadmium, aluminum, indium, tin, ruthenium, cobalt, nickel, palladium, and platinum were specifically exemplified in the general disclosure. Chang et al. also is silent with respect to a halogen component. Zeolite in matrix form is taught, but the zeolite content is restricted to 25 to 75 percent in contradistinction to the 1 to 20 percent of the present invention.

U.S. Pat. No. 4,116,870 (Weisang et al.) discloses a catalyst for the treatment of hydrocarbons comprising a refractory inorganic oxide support, platinum, zirconium or titanium, tin, and a halogen component. The general disclosure teaches a porous alumina or aluminosilicate carrier and possible association of the metals lead, indium, tin, rhenium and germanium with platinum. However, this reference does not suggest the specific zeolitic component of the present catalytic composite.

U.S. Pat. No. 4,152,363 (Tabak et al.) discloses a process for the isomerization of alkylaromatics employing a catalyst containing about 0.1 to 5% zeolite in a binder diluent and a Group VIII metal. However, Tabak is silent with respect to a lead component.

U.S. Pat. Nos. 4,331,822 and 4,485,185 (Onodera et al.) disclose an isomerization process and catalyst composition, respectively. The catalyst comprises a zeolite of the ZSM type and two or more metals, platinum and at least one metal selected from titanium, barium and lanthanum. A preferred embodiment comprises 1 to 99% inorganic oxide binder and the general specification discloses also lead, chromium, zinc, gallium, germanium, strontium, yttrium, zirconium, molybdenum, palladium, tin, cesium, tungsten, osmium, cadmium, mercury, indium and beryllium as the second metal. The broad disclosure of Onodera et al. does not anticipate the specific catalyst composite of the present invention. The prosecution history shows that Onodera et al. teaches away from a halogen component on the catalyst, noting that halogen "has adverse effects" and "is undesirable". Further, Onodera et al. teaches compositing of the metal components with the zeolite in contradistinction to the present invention.

When the prior art is compared with the subject matter of the present invention, it is believed that neither the instant catalyst composition nor the results in isomerizing alkylaromatics are taught or suggested. The unique combination of Group VIII metal, lead, and relatively low pentasil zeolite content on an inorganic binder exhibits surprising results in converting ethylbenzene and isomerizing xylenes while avoiding substantial xylene losses.

DESCRIPTION OF THE INVENTION

Objects

It is an object of the present invention to provide a novel catalyst, useful particularly for the isomerization of alkylaromatics. A corollary objective of the invention is to provide an isomerization process which achieves a near-equilibrium mixture of xylene isomers in the product with high retention of xylenes and effective conversion of ethylbenzene to benzene and ethane.

Summary of the Invention

This invention is based on the discovery that a bound zeolite catalyst with defined ratios of Group VIII metal and lead and metals principally on the binder demonstrates unexpectedly high retention of aromatic rings when isomerizing of a mixture of xylenes and ethylbenzene.

Embodiments

A broad embodiment of the present invention is a catalyst, comprising a Group VIII metal component and a lead component wherein the atomic ratio of lead to Group VIII metal is from about 2 to about 10, from about 1 to about 20 mass % of a pentasil zeolite, and an inorganic binder, wherein from about 80% to about 100% of the Group VIII metal and from about 60% to 100% of the lead components are contained on the inorganic oxide binder.

In a preferred embodiment, the Group VIII metal component comprises platinum and amounts to from about 0.01 to about 2 mass % of the catalyst.

In a highly preferred embodiment, the catalyst comprises a halogen component amounting to from about 0.1 to about 1.0 mass % of the catalyst.

In an even more highly preferred embodiment, the inorganic oxide binder comprises alumina.

In an alternative embodiment directed toward the method of manufacture of the catalyst, the lead component is added to the catalyst along with the Group VIII metal after compositing the pentasil zeolite and the inorganic oxide binder.

In an alternative embodiment, the lead and pentasil zeolite components are first intimately admixed with the inorganic oxide binder prior to forming the shaped catalytic composite.

In an alternative embodiment, an isomerization process utilizes a catalyst comprising a platinum component and a lead component wherein the atomic ratio of lead to platinum of from about 2 to about 10, a chlorine component, from about 1 to about 20 mass % of a pentasil zeolite, and an alumina binder, wherein about 80 to 100% of the Group VIII metal and from about 60 to 100% of the lead component are contained on the inorganic oxide binder to isomerize xylenes and to convert ethylbenzene to principally benzene and ethane.

These as well as other embodiments will become apparent upon a reading of the following detailed description of the invention.

DETAILED DESCRIPTION OF THE INVENTION

To reiterate briefly, one embodiment of the present invention is a catalyst, comprising a metal component from Group VIII of the Periodic Table (see Cotton and Wilkinson, *Advanced Inorganic Chemistry*, (3rd ed., 1972)) metal component, a lead component sufficient to amount to an atomic ratio of lead to Group VIII metal of from about 2 to about 10, from about 1 to about 20 mass % of a pentasil zeolite, and an inorganic binder, wherein from about 80% to about 100% of the Group VIII metal and from about 60% to about 100% of the lead component are contained on the inorganic binder.

As mentioned, the catalyst of the present invention contains a pentasil zeolite. "Pentasil" is a term used to describe a class of shape-selective zeolites. This novel class of zeolites is well known to the art and is typically characterized by a silica/alumina mole ratio of at least about 12. Descriptions of the pentasils may be found in U.S. Pat. Nos. 4,159,282; 4,163,018; and 4,278,565, all of which are incorporated herein by reference. Of the pentasil zeolites, the preferred ones are ZSM-5, ZSM-8, ZSM-11, ZSM-12, ZSM-23, and ZSM-35, with ZSM-5 being particularly preferred. It is a preferred embodiment of the present invention that the pentasil be in the hydrogen form. Conversion of an alkali metal form pentasil to the hydrogen form may be performed by treatment with an aqueous solution of a mineral acid. Alternatively, hydrogen ions can be incorporated into the pentasil by ion exchange with ammonium hydroxide followed by calcination.

The relative proportion of pentasil zeolite in the catalyst composite is an essential feature of the present invention. The pentasil zeolite content may range from about 1 to about 20 mass %, with 5 to 15 mass % preferred. There is a tradeoff between the zeolite content of the catalyst composite and the pressure and temperature of an isomerization operation in maintaining low xylene losses. Higher pressure requires higher temperature and lower zeolite content in order to avoid saturation and subsequent hydrocracking of aromatic compounds. The balance of the three parameters may result in a different optimum zeolite content for an isomerization unit designed after the present invention than for an existing unit with fixed pressure and temperature limitations. Our experimental program shows best results within the pentasil zeolite proportions disclosed hereinabove.

It is also within the scope of the present invention that the particular pentasil selected may be a gallosilicate. Gallosilicates have essentially the same structure as the ZSM-type zeolites described hereinabove, except that all or part of the aluminum atoms in the aluminosilicate crystal framework are replaced by gallium atoms. This substitution of the aluminum by gallium is usually performed prior to or during synthesis of the zeolite. The gallium content for this particular type of pentasil, expressed as mole ratios of $SiO_2$ to $Ga_2O_3$, ranges from 20:1 to 400:1 or more.

Considering next the inorganic oxide binder utilized in the present invention, it is preferred that the binder be a porous, adsorptive, high-surface area support having a surface area of about 25 to about 500 $m^2/g$. The binder should also be uniform in composition and relatively refractory to the conditions utilized in the hydrocarbon conversion process. By the term "uniform in composition", it is meant that the support by unlayered, has no concentration gradients of the species inherent to its composition, and is completely homogeneous in composition. Thus, if the support is a mixture of two or more refractory materials, the relative amounts of these materials will be constant and uniform throughout the entire support. It is intended to include within the scope of the present invention binder materials which have traditionally been utilized in dual-functional hydrocarbon conversion catalysts such as: (1) activated carbon, coke, or charcoal; (2) silica or silica gel, silicon carbide, clays and silicates including those synthetically prepared and naturally occurring, which may or may not be acid treated, for example, attapulgus clay, diatomaceous earth, fuller's earth, kaolin, kieselguhr, etc.; (3) ceramics, porcelain, bauxite; (4) refractory inorganic oxides such as alumina, titanium dioxide, zirconium dioxide, chromium oxide, zinc oxide, magnesia, thoria, boria, silica-alumina, silica-magnesia, chromia-alumina, alumina-boria, silica-zirconia, zirconia-alumina, etc.; and (5) combinations of one or more elements from one or more of these groups. The preferred binders for use in the present invention are refractory inorganic oxides, with best results obtained with a binder comprised of alumina. Suitable aluminas are the crystalline aluminas known as the gamma-, eta-, and theta-aluminas, with gamma-alumina as the preferred form. In addition, in some embodiments, the alumina binder may contain minor proportions of other well known refractory inorganic oxides such as silica, zirconia, magnesia, etc.; however, the preferred binder is substantially pure gamma-alumina. Preferred binders have an apparent bulk density of about 0.3 to about 0.8 g/cc and surface area characteristics such that the average pore diameter is about 20 to 300 angstroms and the pore volume is about 0.1 to about 1 cc/g. In general, excellent results are typically obtained when the binder of the catalyst is gamma-alumina in the form of spherical or extruded particles having a relatively small diameter (i.e., typically about 1/16-inch), an apparent bulk density of about 0.4–0.7 g/cc, a pore volume of about 0.7 cc/g, and a surface area of about 200–270 $m^2/g$.

The preferred alumina binder is uniform in composition and may be prepared in any suitable manner and may be synthetically prepared or naturally occurring. Whatever type of alumina is employed, it may be activated prior to use by one or more treatments including drying, calcination, steaming, etc., and it may be in a form known as activated alumina, activated alumina of commerce, porous alumina, alumina gel, etc. For example, the alumina binder may be prepared by adding a suitable alkaline reagent, such as ammonium hydroxide to a salt of aluminum such as aluminum chloride, aluminum nitrate, etc., in an amount to form an aluminum hydroxide gel which, upon drying and calcining, is converted to alumina.

Using techniques commonly known to those skilled in the art, the catalyst of the present invention may be composited and shaped into any useful form such as spheres, pills, cakes, extrudates, powders, granules, tablets, etc., and utilized in any desired size. These shapes may be prepared utilizing any known forming operations including spray drying, tabletting, spherizing, extrusion, and nodulizing. A preferred shape for the catalyst composite is the extrudate prepared using the well-known extrusion method. Here the pentasil zeolite is combined with the binder and a suitable peptizing agent and mixed to form a homogeneous dough or thick paste. The lead component can be added to the binder before compositing or to the mixture before shaping, either before, after, or simultaneously with the pentasil zeolite, in one embodiment as discussed later in more detail. This material is then extruded through a die pierced with multiple holes and the spaghetti-shaped extrudate is cut off on the opposite side to form short cylinders. The rheological properties of the dough mixture can be varied by the use of "extrusion aids" such as methylcellulose, stearates, small amounts of clay, colloidal silica, etc. After extrusion, the cylinders are dried and calcined as set forth hereinbelow.

An alternative preferrd shape of the subject catalytic composite is the sphere, manufactured by the well-known oil drop method which comprises forming a hydrosol of the desired inorganic oxide binder by any of the techniques taught in the art. For example, alumina hydrosol is preferably prepared by reacting aluminum metal with hydrochloric acid. The pentasil zeolite is then uniformly dispersed in the hydrosol. This resultant zeolite-containing hydrosol is then commingled with a suitable gelling agent and is dispersed as droplets into an oil bath maintained at elevated temperatures. As discussed later, in one embodiment, the lead component may be added to the mixture prior to forming the droplets and either before, after, or simultaneously with the pentasil. The droplets of the mixture remain in the oil bath until they set and form hydrogel spheres. The spheres are continuously withdrawn from the oil bath and typically subjected to specific aging treatments in oil and an ammoniacal solution to further improve their physical characteristics. The resulting aged and gelled particles are then washed and dried at a relatively low temperature of about 100°–205° C. and subjected to a calcination procedure at a temperature of about 450°–700° C. for a period of about 1 to about 20 hours. See the teachings of U.S. Pat. No. 2,620,314 for additional details.

Another component of the present invention is the Group VIII metal. Preferably this Group VIII metal is selected from the platinum-group metals, which include platinum, palladium, rhodium, ruthenium, osmium, and iridium. The preferred platinum-group component is platinum, with palladium being the next preferred metal. The platinum-group component may exist within the final catalyst composite as a compound such as an oxide, sulfide, halide, oxysulfide, etc., or as an elemental metal or in combination with one or more other ingredients of the catalyst. It is believed that the best results are obtained when substantially all the platinum-group component exists in a reduced state. The platinum-group component generally comprises from about 0.01 to about 2 mass % of the final catalytic composite, calculated on an elemental basis. It is preferred that the platinum content of the catalyst be between about 0.05 and 1 mass %.

The platinum-group component may be incorporated into the catalyst composite in any suitable manner resulting in the disclosed distribution of metal between zeolite and binder, such as by ion-exchange or impregnation of the zeolite/binder composite. The preferred method of preparing the catalyst normally involves the utilization of a water-soluble, decomposable compound of a platinum-group metal to impregnate the calcined zeolite/binder composite. For example, the platinum-group component may be added to the calcined hydrogel by commingling the calcined composite with an aqueous solution of chloroplatinic or chloropalladic acid.

Another essential constituent of the present invention is a lead component. The lead component may be incorporated into the catalytic composite in any suitable manner to effectively disperse this component on the individual moieties of the composite and to achieve the disclosed distribution of lead between the zeolite moiety and the binder moiety. Suitable methods could include coprecipitation or cogelation with the inorganic oxide binder with or without the zeolite, ion-exchange with the inorganic oxide binder, or impregnation of the catalyst at any stage in the preparation. One preferred method of incorporating the lead component into the catalytic composite involves the addition of suitable soluble lead compounds such as lead nitrate, lead acetate, lead citrate, lead formate, and the like to the zeolite-containing hydrosol of the inorganic oxide, and then combining the hydrosol with a suitable gelling agent and dispersing the resulting mixture into an oil bath with subsequent processing as explained in more detail hereinabove. After calcining the gelled hydrosol, there is obtained a binder material having a uniform dispersion of lead oxide in an intimate combination principally with the inorganic oxide binder. Another preferred method of incorporating the lead component into the catalyst composite involves the utilization of a soluble, decomposable compound of lead to impregnate and uniformly disperse the lead on the composite. Best results are ordinarily obtained with a solution of lead nitrate and nitric acid. In general, the lead component can be impregnated either prior to, simultaneously with, or after the platinum-group metallic component is added to the carrier material. A preferred method is to impregnate the lead component simultaneously with the platinum-group component. A preferred impregnation solution contains chloroplatinic acid, nitric acid, and lead nitrate.

Regardless of which lead compound is used in the preferred impregnation step, it is important that the lead component be uniformly distributed throughout the carrier material. That is, it is important that the concentration of lead in any reasonably divisible portion of the carrier material be approximately the same. In order to achieve this objective, it is necessary to maintain the pH of the impregnation solution in a range of from 7 to about 1 or less. Good platinum-lead interaction results when the nitric acid content of the impregnated carrier material is from about 3 to about 15 mass %, and a nitric acid content from about 5 to about 11 mass % is preferred.

The effective dispersion of the Group VIII metal and lead components is essential to obtain the selectivity demonstrated by the catalyst of the present invention. It is believed, without limiting the present invention, that effective dispersion of the metals and avoidance of platinum crystallites results in association of the Group VIII metal and lead with resulting beneficial attenuation of the activity of the Group VIII metal. Such attenuation is believed to enhance catalyst selectivity by reducing xylene losses. Optimum interaction between Group VIII metal and lead components has been estimated for a large number of catalyst formulations and preparation techniques using a microreactor test of the conversion of methylcyclohexane to toluene at 450° C. and 1 atm. pressure, with 1–40% conversion, and preferably 10–30% conversion being a target value.

It is essential to fix the amount of the lead component as a function of the amount of Group VIII metal contained in the catalyst composite. More specifically, unanticipated beneficial interaction of the Group VIII metal component and lead component is effected at an atomic ratio of lead to Group VIII metal of from about 2:1 to 10:1. Best results are obtained at an atomic ratio of lead to Group VIII metal from about 3:1 to about 5:1.

A preferred constituent of the bimetallic catalyst used in the present invention is the halogen component. Although the precise form of the chemistry of the association of the halogen component with the carrier material is not entirely known, it is customary in the art to refer to the halogen component as being combined with the carrier material or with the other ingredients of the catalyst in the form of the corresponding halide (e.g. as the chloride or the fluoride). This combined halogen may be either fluorine, chlorine, iodine, bromine, or mixtures thereof. Of these, fluorine and, particularly, chlorine are preferred. The halogen may be added to the carrier material in any suitable manner either during preparation of the carrier material or before or after the addition of the other components.

For example, the halogen may be added at any stage of the preparation of the carrier material or to the calcined carrier material as an aqueous solution of a suitable decomposable halogen-containing compound such as hydrogen fluoride, hydrogen chloride, hydrogen bromide, ammonium chloride, etc. The halogen component or a portion thereof may be combined with the carrier material during the impregnation of the latter with the platinum-group component; for example, through the utilization of a mixture of chloroplatinic acid and hydrogen chloride. In another situation, the alumina hydrosol which is one of the hereinabove preferred methods to form the alumina carrier material may contain halogen and thus contribute at least a portion of the halogen component to the final composite. In a preferred embodiment, halogen is included in the air atmosphere utilized during the final calcination step to promote dispersion of the Group VIII metal and lead components. The halogen is combined with the carrier material to result in a final composite that contains from about 0.1 to about 1.0 mass % halogen, calculated on an elemental basis.

Regardless of the details of how the components of the catalyst are combined with the porous carrier material, the catalyst composite will be dried at a temperature of from about 100° to about 320° C. for a period of from about 2 to about 24 or more hours. The dried composite is finally calcined at a temperature of from about 400° to about 600° C. in an air atmosphere for a period of from about 0.1 to about 10 hours to convert the metallic compounds substantially to the oxide form. The chloride content of the catalyst is adjusted by including a halogen or halogen-containing compound in the air atmosphere. The use of both chlorine and hydrogen chloride is particularly preferred.

The resultant calcined composite is subjected to a substantially water-free reduction step prior to its use in the conversion of hydrocarbons. This step is designed to insure a uniform and finely divided dispersion of the metallic components. Preferably, substantially pure and dry hydrogen (i.e., less than 20 vol. ppm $H_2O$) is used as the reducing agent in this step. The reducing agent contacts the catalyst at conditions, including a temperature of from about 200° to about 650° C. and for a period of from about 0.5 to about 10 hours, effective to reduce substantially all of the Group VIII metal component to the metallic state.

Isomerization Process

The catalyst of this invention finds utility in the isomerization of isomerizable alkylaromatic hydrocarbons of the general formula $C_6H_{(6-n)}R_n$, where n is an integer from 2 to 5 and R is $CH_3$, $C_2H_5$, $C_3H_7$, or $C_4H_9$, in any combination and including all the isomers thereof. Preferred isomerizable alkylaromatic hydrocarbons include the xylene isomers in admixture with ethylbenzene as a nonequilibrium mixture.

The isomerizable alkylaromatic hydrocarbons may be utilized as found in selective fractions from various refinery petroleum streams, e.g., as recovered from catalytic reformate by fractionation or solvent extraction, produced as a by-product of pyrolysis of petroleum distillates to obtain principally light olefins, or recovered from cracking of heavy petroleum fractions principally to gasoline-range products. The isomerizable aromatic hydrocarbons which are converted in the process of this invention need not be concentrated. By increasing the yield of valuable petrochemical intermediates from streams which otherwise could command only fuel value, the profitability of such petrochemical operations can be enhanced.

According to the process of the present invention, an alkylaromatic hydrocarbon charge stock, preferably in admixture with hydrogen, is contacted with a catalyst of the type hereinbefore described in an alkylaromatic hydrocarbon isomerization zone. Contacting may be effected using the catalyst in a fixed-bed system, a moving-bed system, a fluidized-bed system, or in a batchtype operation. In view of the danger of attrition loss of the valuable catalyst and of operational advantages, it is preferred to use a fixed-bed system. In this system, a hydrogen-rich gas and the charge stock are preheated by suitable heating means to the desired reaction temperature and then passed into an isomerization zone containing a fixed bed of the catalyst previously characterized. The conversion zone may be one or more separate reactors with suitable means therebetween to ensure that the desired isomerization temperature is maintained at the entrance to each zone. It is to be noted that the reactants may be contacted with the catalyst bed in either upward, downward, or radial flow fashion, and that the reactants may be in the liquid phase, a mixed liquidvapor phase, or a vapor phase when contacted with the catalyst.

The process of this invention for isomerizing an isomerizable alkylaromatic hydrocarbon is preferably effected by contacting the alkylaromatic, in a reaction zone containing the hereinbefore described catalyst, with a fixed catalyst bed by passing the hydrocarbon in a down-flow fashion through the bed while maintaining the zone at proper alkylaromatic isomerization conditions such as a temperature in the range of from about 0° to about 600° C. and a pressure of from atmospheric to about 100 atmospheres. Preferably, a temperature range of about 350°-500° C. and a pressure range of 2-30 atmospheres is employed. The hydrocarbon is passed into the reaction zone, preferably in admixture with hydrogen, at a hydrogen to hydrocarbon mole ratio of about 0.5:1 to about 15:1 or more. Other inert diluents such as nitrogen, argon, methane, ethane, and the like may be present. The liquid hourly hydrocarbon space velocity of the feed relative to the volume of catalyst is from about 0.5 to about 30 hr$^{-1}$, and most preferably at 1 to 20 hr$^{-1}$.

The particular product recovery scheme employed is not deemed to be critical to the instant invention. Any recovery scheme known in the art may be used. Typically, the reactor effluent will be condensed with the hydrogen and light hydrocarbon components removed therefrom by flash separation. The condensed liquid product is then subjected to a fractionation procedure to further purify the desired liquid product. Valuable high-purity benzene can be recovered from the light liquid product. In some instances it may be desirable to recover certain product species, such as ortho-xylene, by more rigorous fractionation. In most instances the liquid xylene product is processed to selectively recover the para-xylene isomer. Recovery of para-xylene can be performed by crystallization methods of most preferably by selective adsorption using crystalline aluminosilicates. The raffinate remaining after recovery of the desired xylene isomers may be returned to the isomerization reactor section.

BRIEF DESCRIPTION OF THE DRAWING

The accompanying drawing shows the surprising benefit of the subject invention. The "Graph" illustrates the relationship between ethylbenzene conversion and aromatic-ring loss for four catalysts of the invention in comparison to two catalysts not of the invention. The catalysts and comparison are described in the following examples.

EXAMPLES

The following examples will serve to illustrate certain specific embodiments of the present invention. These examples should not, however, be construed as limiting the scope of the invention as set forth in the claims. There are many possible other variations, as those of ordinary skill in the art will recognize, which are within the spirit of the invention.

Two catalysts of the prior art and four of the present invention were prepared as described hereinafter and evaluated for isomerization of $C_8$ aromatics. These catalysts were prepared and tested as part of the development program of the present invention, and the comparison is appropriate in order to identify the benefits of the invention. The comparison is based on xylene loss at a standard 65% ethylbenzene conversion and aromatic-ring loss over a range of conversions.

EXAMPLE 1

Catalyst A represents a catalyst of the prior art. This catalyst consisted essentially of approximately 11 mass % hydrogen-form ZSM-5 zeolite and 0.29 mass % platinum, with the remainder being alumina binder. The zeolite was added to an alumina sol solution, prepared by digesting metallic aluminum in hydrochloric acid, in an amount sufficient to yield a zeolite content in the finished catalyst of about 11 mass %. A second solution of hexamethylenetetramine (HMT) was prepared and added to the zeolite/alumina sol mixture to give homogeneous admixture. This admixture was then dispersed as droplets into an oil bath maintained at about 93° C. The droplets remained in the oil bath at 150° C. until they set and formed hydrogel spheres. These spheres were removed from the oil bath, water washed with a 0.5% ammonia/water solution, air dried, and calcined at a temperature of about 650° C. These calcined spheres were then impregnated with a solution of chloroplatinic acid with 2 mass % hydrochloric acid to yield a final platinum level of 0.29 mass % on the finished catalyst. The impregnated spheres were oxidized and chloride adjusted at 525° C. to yield 0.68 mass % chloride on the catalyst, subjected to a reducing environment of $H_2$ at 565° C., and sulfided with $H_2S$ to yield 0.07 mass % sulfur on the catalyst.

The catalyst was evaluated for isomerization of $C_8$ aromatics in a pilot plant. The feedstock composition was approximately as follows in mass %:

| | |
|---|---|
| benzene | 0.1 |
| toluene | 0.6 |
| paraxylene | 3.6 |
| metaxylene | 68.1 |
| orthoxylene | 16.9 |
| ethylbenzene | 10.3 |
| $C_9$ hydrocarbons | 0.4 |

Pilot-plant operating conditions comprised a temperature range of about 390°-460° C., a pressure range of 4-14 atmospheres, and liquid hourly space velocities of 4-8 hr$^{-1}$. The temperature and space velocity were varied within these ranges to develop the relationship between ethylbenzene conversion and product yield, as discussed below and illustrated in the drawing. The pressure was varied along with the temperature to avoid excessive hydrogenation of $C_8$ aromatics.

At a standard 65% conversion of ethylbenzene, Catalyst A shows about 4.6 mole % xylene loss. Aromatic-ring losses for Catalyst A are shown in the Graph.

EXAMPLE 2

Catalyst B was another catalyst not of the invention, and consisted of approximately 10 mass % hydrogen-form ZSM-5 zeolite, 0.29 mass % platinum, 0.32 mass % lead, and 0.73 mass % chloride, with the remainder being alumina binder. The lead/platinum atomic ratio thus was about 1.0:1. The spherical catalyst was prepared by the oil-drop method in the same manner as Catalyst A, with the lead added as $Pb(NO_3)_2$ by coimpregnation along with platinum of the calcined zeolite/alumina composite. The impregnated spheres were oxidized, chloride-adjusted and reduced in $H_2$ in the same manner as Catalyst A.

Catalyst B was evaluated for isomerization of $C_8$ aromatics in the same manner and using the feedstock as for Catalyst A. Xylene loss at 65% ethylbenzene conversion was about 2.2 mole %. Aromatic-ring losses for Catalyst B are shown in the Graph.

EXAMPLE 3

Catalyst C was prepared in accordance with the invention, and consisted essentially of about 11 mass % hydrogen-form ZSM-5 zeolite, 0.21 mass % platinum, 0.76 mass % lead, and 0.91 mass % chloride, with the remainder being alumina binder. The lead/platinum atomic ratio thus was about 3.4:1. The composite was extruded, by means known in the art, prior to impregnation of platinum and lead.

Distribution of platinum and lead between the zeolite and binder was investigated by Scanning Transmission Electron Microscope to determine an elemental analysis from the sub-micron region. The extrudates were ground, placed on a carbon-coated copper grid, and inserted into the VG-HB-5 dedicated STEM. Results were approximately as follows:

|  | % on Zeolite | % on $Al_2O_3$ |
| --- | --- | --- |
| Platinum | 1–2 | 98–99 |
| Lead | 14 | 86 |

Pilot-plant testing of Catalyst C in the same manner and using the same feedstock as for Catalysts A and B showed xylene loss at 65% ethylbenzene conversion of about 0.8 mole %, or more than 80% better (lower) than for Catalyst A and more than 60% better than for Catalyst B. The performance of Catalyst C for retention of aromatic rings is compared to that of Catalysts A and B in the Graph over a range of ethylbenzene conversions.

EXAMPLE 4

Catalyst D was prepared in accordance with the invention, and consisted essentially of about 7 mass % hydrogen-form ZSM-5 zeolite, 0.16 mass % platinum, 0.77 mass % lead, and 0.91 mass % chloride, with the remainder being alumina binder. The lead/platinum atomic ratio thus was about 4.5:1. The catalyst was prepared by the oil-drop method in the same manner as Catalyst B. Nitric acid was employed in the coimpregnation of lead and platinum. Catalyst D thus contained less of the higher-cost zeolite component than Catalysts A, B or C.

In pilot-plant testing comparable to Catalysts A, B and C, Catalyst D showed xylene loss at 65% ethylbenzene conversion of about 1.5 mole %. This loss, compared at the same ethylbenzene conversion to the two catalysts of the prior art, was about one-third that of Catalyst A and more than 30% less than that of Catalyst B. Aromatic-ring losses for Catalyst D are shown in the Graph.

EXAMPLE 5

Two catalysts were prepared which illustrate alternative methods of incorporating the lead component, and their performance was compared in pilot-plant tests.

Catalyst E was prepared in accordance with the invention, and consisted essentially of about 11 mass % hydrogen-form ZSM-5 zeolite, 0.14 mass % platinum, 0.47 mass % lead, and 0.81 mass % chloride, with the remainder being alumina binder. The lead/platinum atomic ratio thus was about 3.2:1. The composite was extruded, by means known in the art, prior to impregnation of platinum and lead. Nitric acid was employed in the coimpregnation of lead and platinum.

Catalyst F was prepared in accordance with the invention, and consisted essentially of about 11 mass % hydrogen-form ZSM-5 zeolite, 0.079 mass % platinum, 0.38 mass % lead, and 0.73 mass % chloride, with the remainder being alumina binder. The lead/platinum atomic ratio thus was about 4.5:1. The catalyst was prepared by incorporating lead nitrate into the zeolite-containing hydrosol of the alumina binder. The composite was extruded by means known in the art prior to the impregnation of platinum.

Catalysts E and F, embodying alternative methods of incorporating the lead component, show essentially identical results. Xylene losses at 65% ethylbenzene conversion are about 1.5 mole %, or 30% better than prior-art Catalyst B. Aromatic-ring losses are shown in the Graph.

EXAMPLE 6

Aromatic-ring losses are compared in the Graph for the two catalysts of the prior art and the four catalysts of the invention described hereinabove. Aromatic-ring loss is a measure of the yield of valuable product from an isomerization process, as aromatics retained through the isomerization process generally are recovered as valuable para-xylene or benzene in subsequent processing. Aromatic-ring losses are shown graphically against ethylbenzene conversion, which is a measure of isomerization cost in that unconverted ethylbenzene generally builds up in a recycle loop to the isomerization process from downstream recovery facilities.

The Graph shows improvement by a factor of two to three in aromatic-ring losses for a prior-art platinum-lead catalyst over a catalyst of the prior art not containing lead. Catalysts of the present invention unexpectedly and astonishingly show an order-of-magnitude improvement and near-elimination of aromatic-ring losses.

We claim as our invention:

1. A catalyst for the isomerization of isomerizable alkylaromatic hydrocarbons comprising a combination of a group VIII metal component and a lead component with a carrier material containing about 1 to about 20 mass % of a pentasil zeolite and an inorganic oxide binder, wherein the atomic ratio of lead to Group VIII metal is about 2 to about 10 and wherein about 80% to about 100% of the Group VIII metal component and about 60% to about 100% of the lead component are combined with the inorganic oxide binder.

2. The catalyst of claim 1 wherein said catalyst comprises a halogen component.

3. The catalyst of claim 1 wherein the halogen component comprises a chlorine component in an amount of about 0.1 to about 1.0 mass % of the catalyst.

4. The catalyst of claim 1 wherein the pentasil zeolite comprises from about 5 to about 15 mass % of the carrier material.

5. The catalyst of claim 1 wherein the pentasil zeolite is selected from the Group consisting of ZSM-5, ZSM-8, ZSM-11, ZSM-12, ZSM-23, ZSM-35, and ZSM-38.

6. The catalyst of claim 1 wherein the pentasil zeolite is ZSM-5.

7. The catalyst of claim 1 wherein the inorganic oxide binder comprises gamma-alumina.

8. The catalyst of claim 1 wherein the Group VIII metal component comprises platinum in an amount of about 0.01 to 2 mass % of the catalyst.

9. The catalyst of claim 1 wherein the atomic ratio of lead to Group VIII metal is about 3 to about 5.

10. A method of preparing the catalyst of claim 1 comprising simultaneous deposition of the lead component and the Group VIII metal component upon the carrier material.

11. A method of preparing the catalyst of claim 1 comprising intimate admixing of the lead component with the pentasil zeolite and the inorganic oxide binder during preparation of the carrier material prior to forming the shaped composite particles.

12. An isomerization catalyst for the isomerization of a non-equilibrium mixture of xylenes and conversion of ethylbenzene, consisting essentially of a combination of about 0.01 to about 2 mass % platinum, a lead component and about 0.1 to about 1.0 mass % of a chlorine component with a carrier material containing about 1 to about 20 mass % of a pentasil zeolite and an inorganic oxide binder, wherein the atomic ratio of lead to platinum is from about 3 to about 5 and wherein from about 80 to about 100% of the platinum component and from about 60 to about 100% of the lead component are combined with the inorganic oxide binder.

* * * * *